US00PP14705P2

(12) United States Plant Patent
Rietvink

(10) Patent No.: US PP14,705 P2
(45) Date of Patent: Apr. 20, 2004

(54) DELPHINIUM PLANT NAMED 'DELFT BLUE'

(50) Latin Name: *Delphinium belladona*
Varietal Denomination: Delft Blue

(75) Inventor: Cornelis Rietvink, Noordwijkerhout (NL)

(73) Assignee: Witteman & Co., Hillegom (NL)

( * ) Notice: Subject to any disclaimer, the term of this patent is extended or adjusted under 35 U.S.C. 154(b) by 0 days.

(21) Appl. No.: 10/437,947

(22) Filed: May 13, 2003

(51) Int. Cl.[7] ..... A01H 5/00
(52) U.S. Cl. ..... Plt./263
(58) Field of Search ..... Plt./263, 320

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Delphinium plant named 'Delft Blue', characterized by its upright plant habit; freely flowering habit; and blue and light blue bi-colored flowers.

2 Drawing Sheets

Botanical classification/cultivar designation: *Delphinium belladona* cultivar Delft Blue.

BACKGROUND OF THE INVENTION

The present Invention relates to a new and distinct cultivar of Delphinium plant, botanically known as *Delphinium belladona*, and hereinafter referred to by the name 'Delft Blue'.

The new Delphinium was discovered by the Inventor in 1999 in a controlled environment in Noordwijkerhout, The Netherlands, as a naturally-occurring whole plant mutation of the *Delphinium belladona* cultivar Volkerfrieden, not patented. The new Delphinium was selected by the Inventor on the basis of its unique blue and light blue bi-colored flowers.

Asexual reproduction of the new Delphinium by cuttings in a controlled environment in Noordwijkerhout, The Netherlands, since 2000, has shown that the unique features of this new Delphinium are stable and reproduced true to type in successive generations.

SUMMARY OF THE INVENTION

Plants of the cultivar Delft Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Delft Blue'. These characteristics in combination distinguish 'Delft Blue' as a new and distinct cultivar:

1. Upright plant habit.
2. Freely flowering habit.
3. Blue and light blue bi-colored flowers.

Plants of the cultivar Delft Blue differ from the parent cultivar, Volkerfrieden and other Delphinium cultivars known to the Inventor in its unique flower coloration.

BRIEF DESCRIPTION OF THE PHOTOGRAPHS

The accompanying colored photographs illustrate the overall appearance of the new Delphinium, showing the colors as true as it is reasonably possible to obtain in colored reproductions of this type. Colors in the photographs may differ slightly from the color values cited in the detailed botanical description which accurately describe the colors of the new Delphinium.

The photograph on the first sheet comprises a side perspective view of a typical flowering plant of 'Delft Blue' grown in a container.

The photograph at the top of the second sheet is a close-up view of typical flowers of 'Delft Blue'.

The photograph at the bottom of the second sheet is a close-up view of the upper surface of a typical leaf of 'Delft Blue'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about two years old and grown under outdoor field conditions which closely approximate commercial production conditions in Hillegom, The Netherlands. During the production of the plants, day temperatures ranged from 18 to 32° C. and night temperatures ranged from 10 to 18° C. The photographs and description were taken in August, 2002.

Botanical classification: *Delphinium belladona* cultivar Delft Blue.

Parentage: Naturally-occurring whole plant mutation of the *Delphinium belladona* cultivar Volkerfrieden, not patented.

Propagation:

*Type cutting.*—By cuttings.

*Time to initiate roots.*—About 14 days at 14° C.

*Time to produce a rooted cutting.*—About 40 days at 20° C.

*Root description.*—Fine.

Plant description:

*Form.*—Upright perennial flowering plant with single flowers arranged on racemes; numerous flower racemes per plant; moderately vigorous growth habit.

*Plant height*.—About 100 cm.

*Plant diameter*.—About 60 cm.

*Primary flowering stems*.—Quantity: About three per plant. Length: About 100 cm. Diameter: About 2.5 mm. Internode length: About 6.5 cm. Strength: Strong. Texture: Smooth. Color: 143A to 143B.

*Foliage description*.—Arrangement: Rosette at the base and alternate along flowering stems; simple. Length: About 15.4 cm. Width: About 17.4 cm. Shape: Deeply pedately-lobed. Apex: Acute. Base: Hastate. Margin: Incised to laciniate. Texture: Upper surface: Glabrous. Lower surface: Sparse pubescence at veins. Venation pattern: Laciniate. Color: Young foliage, upper surface: 137B. Young foliage, lower surface: 138B. Fully expanded foliage, upper surface: 139A. Fully expanded foliage, lower surface: 138B. Venation, upper surface: 143A. Venation, lower surface: 143B to 143C. Petiole: Length: About 14.6 cm. Diameter: About 3 mm. Texture, upper and lower surfaces: Sparsely pubescent. Color: 143B to 143C.

Flower description:

*Appearance*.—Single flowers arranged in terminal racemes; flowers zygomorphic. Flowers face mostly outward. Flowers not persistent.

*Quantity of flowers*.—About 15 racemes with about 12 flowers each.

*Natural flowering season*.—Flowering continuous from July through September in The Netherlands.

*Fragrance*.—None detected.

*Flower longevity on the plant*.—About ten days.

*Flower longevity as a cut flower*.—At least ten days.

*Inflorescence size*.—Length: About 26 cm. Diameter: About 11 cm.

*Flower size*.—Diameter: About 4.2 cm. Depth, excluding spur: About 3.7 cm.

*Flower buds*.—Length, including spur: About 3 cm. Diameter: About 7 mm. Shape: Ovoid. Color: 145C; towards the apex, 143A.

*Petals/petaloids*.—Appearance/arrangement: About four petals per flower arranged in a single whorl. Length: Upper petals: About 1.1 cm. Lower petals: About 1 cm. Width: Upper petals: About 4 mm. Lower petals: About 6 mm. Shape: Upper petals: Narrowly spatulate to almost oblong. Lower petals: Spatulate to flabellate. Apex: Upper petals: Obtuse. Lower petals: Emarginate. Margin, upper and lower petals: Entire. Texture: Upper petals: Smooth. Lower petals: Pubescent. Color: Upper petals: When opening and fully opened, upper surface: Between 93A and 96A. When opening and fully opened, lower surface: 96A; towards the base, 93B. Lower petals: When opening and fully opened, upper surface: 93A; towards the apex, 96A; at the center, yellow, 5A to 5B, hairs. When opening and fully opened, lower surface: 93A; towards the apex, 96A.

*Sepals*.—Quantity/arrangement: Five per flower; rotate. Length: Upper and lower sepals: About 2.3 cm. Lateral sepals: About 2.2 cm. Width: Upper and lateral sepals: About 1.4 cm. Lower sepals: About 1.2 cm. Shape, all sepals: Obovate to elliptic. Apex, all sepals: Obtuse. Base, all sepals: Cuneate. Margin, all sepals: Entire. Color, all sepals: When opening and fully opened, upper surface: 100A; towards the margins, 101B to 100D; spot near the apex, 147B. When opening and fully opened, lower surface: 96B to 96C; towards the margins, 97A to 97B; spot near the apex, 147A to 147B. Spur: Arrangement: On uppermost sepal, downwardly bending. Length: About 2.5 cm. Diameter: About 1 mm. Color: Upper surface: 92B to 92C. Lower surface: Towards the base, 92B; towards the apex, 93A.

*Pedicel*.—Length: About 4.5 cm. Diameter: About 1 mm. Angle: About 65 to 75° from vertical. Strength: Strong. Texture: Smooth. Color: 143A to 143B.

*Reproductive organs*.—Stamens: Quantity: About 30 per flower. Anther length: About 1.5 mm. Anther shape: Oblong. Anther color: Darker than 197A. Pollen amount: Scarce to moderate. Color: 157A to 157B. Pistils: Quantity: About three per flower. Pistil length: About 8 mm. Stigma shape: Two-parted. Stigma color: Close to 157D. Style length: About 7.5 mm. Style color: 157B. Ovary color: 137C to 137D.

*Seed/fruit*.—Seed and fruit development has not been observed.

Disease/pest resistance: Plants of the new Delphinium have not been noted to be resistant to pathogens and pests common to Delphinium.

It is claimed:

1. A new and distinct cultivar of Delphinium plant named 'Delft Blue', as illustrated and described.

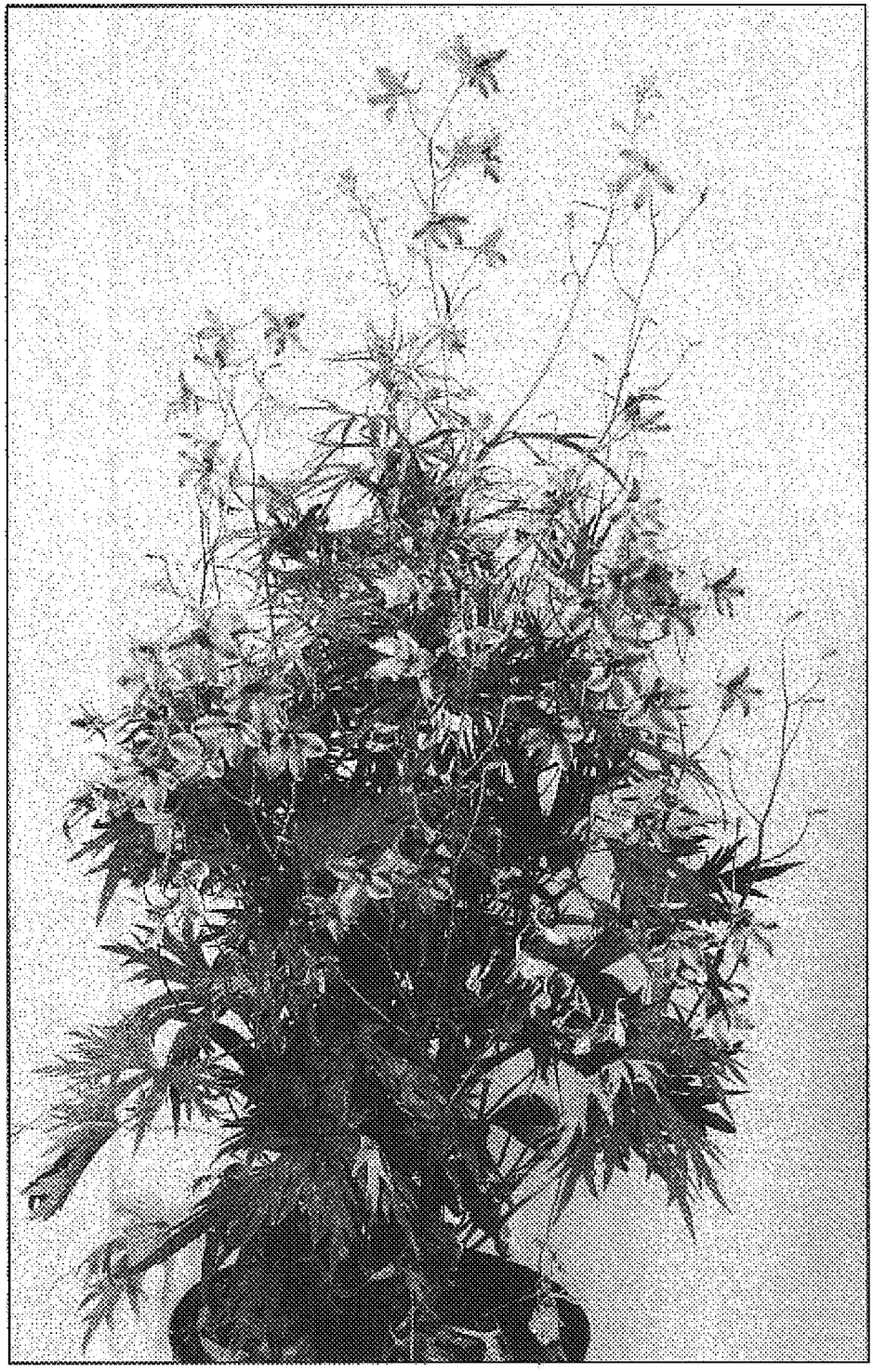

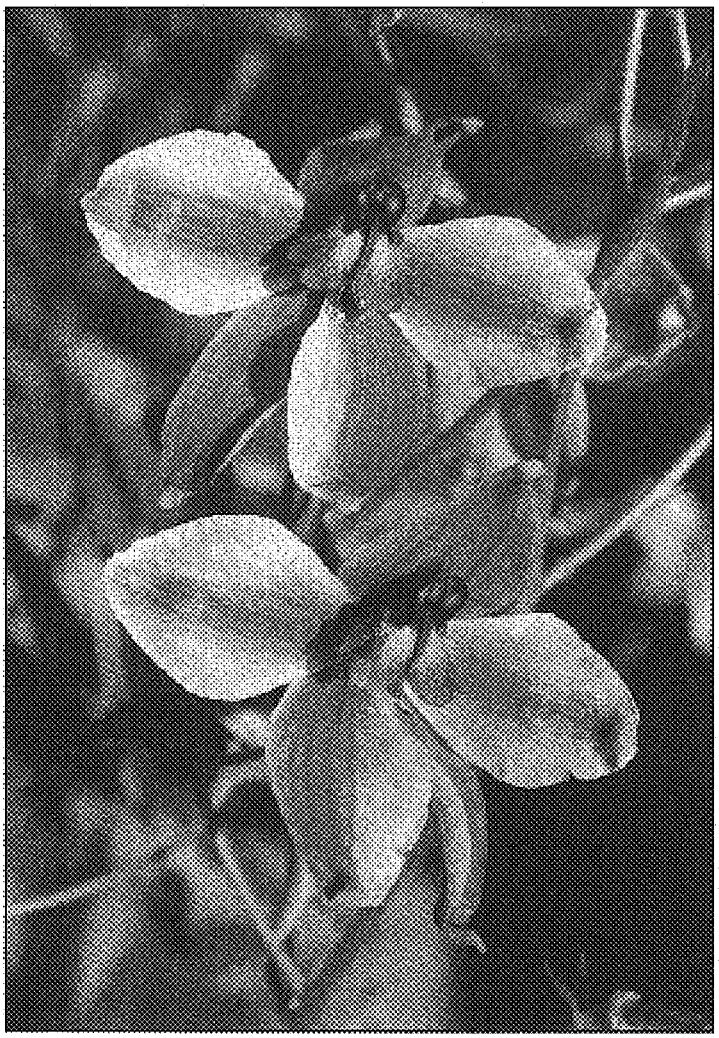
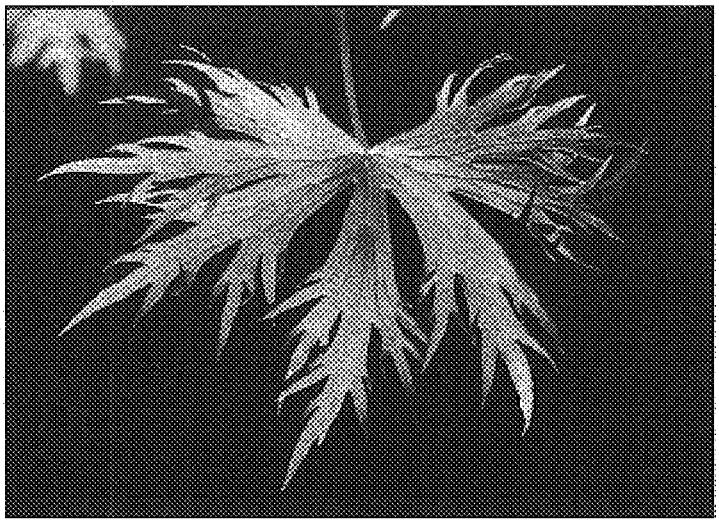

* * * * *